United States Patent [19]

Proctor

[11] Patent Number: 5,330,525
[45] Date of Patent: Jul. 19, 1994

[54] EPICARDIAL LEAD HAVING DUAL ROTATABLE ANCHORS

[75] Inventor: Keith J. Proctor, Lino Lakes, Minn.

[73] Assignee: Medtronic, Inc., Minneapolis, Minn.

[21] Appl. No.: 55,128

[22] Filed: Apr. 29, 1993

[51] Int. Cl.⁵ .............................................. A61N 1/05
[52] U.S. Cl. .................................................. 607/130
[58] Field of Search ................ 128/642; 607/110, 126, 607/128, 129, 130, 131, 132

[56] References Cited

U.S. PATENT DOCUMENTS

| | | |
|---|---|---|
| 3,244,174 | 4/1966 | Wesbey et al. . |
| 3,416,534 | 12/1968 | Quinn . |
| 3,472,234 | 10/1969 | Tachick . |
| 3,814,104 | 6/1974 | Irnich et al. .................. 607/128 |
| 4,142,530 | 3/1979 | Wittkampf . |
| 4,144,890 | 3/1979 | Hess . |
| 4,149,542 | 4/1979 | Thoren . |
| 4,151,835 | 5/1979 | Showell et al. ................ 128/642 |
| 4,177,818 | 12/1979 | De Pedro . |
| 4,258,725 | 3/1981 | O'Neill . |
| 4,294,258 | 10/1981 | Bernard ......................... 128/635 |
| 4,469,104 | 9/1984 | Peers-Trevarton . |
| 4,506,680 | 3/1985 | Stokes . |
| 4,572,605 | 2/1986 | Hess ............................. 339/177 R |
| 4,577,642 | 3/1986 | Stokes . |
| 4,603,704 | 8/1986 | Mund et al. . |
| 4,606,118 | 8/1986 | Cannon et al. .................... 29/825 |
| 4,677,989 | 7/1987 | Robblee . |
| 4,711,251 | 12/1987 | Stokes . |
| 4,773,433 | 9/1988 | Richter et al. . |
| 4,784,160 | 11/1988 | Szilagyi . |
| 4,784,161 | 11/1988 | Skalsky et al. . |
| 4,819,661 | 4/1989 | Heil, Jr. et al. . |
| 4,819,662 | 4/1989 | Heil, Jr. et al. . |
| 4,898,173 | 2/1990 | Daglow et al. . |
| 4,951,687 | 8/1990 | Ufford et al. . |
| 5,007,435 | 4/1991 | Doan et al. . |
| 5,070,605 | 12/1991 | Daglow et al. ...................... 29/842 |
| 5,179,962 | 1/1993 | Dutcher et al. ................ 128/642 X |
| 5,183,043 | 2/1993 | Band et al. ......................... 128/642 |

FOREIGN PATENT DOCUMENTS

| | | | |
|---|---|---|---|
| 1026765 | 7/1983 | U.S.S.R. ............................ 128/642 |
| 1316072 | 1/1971 | United Kingdom .............. 128/642 |
| 1523263 | 8/1978 | United Kingdom .............. 128/642 |
| 2042898 | 10/1980 | United Kingdom .............. 128/642 |
| 8911820 | 12/1989 | World Int. Prop. O. .......... 128/642 |

*Primary Examiner*—Lee S. Cohen
*Assistant Examiner*—Jeffrey R. Jastrzab
*Attorney, Agent, or Firm*—Michael J. Jaro; Reed A. Duthler; Harold R. Patton

[57] ABSTRACT

An epicardial lead having an electrode extending from the bottom thereof in combination with an anchoring system adapted to secure the lead to the heart without the use of complex procedures or tools. In a preferred embodiment the epicardial lead comprises an electrode body having two oppositely disposed arms, each arm fixed for rotation, each arm having an arcuate anchor mounted to the bottom surface, each arcuate anchor having as the center of the arcuate shape the axis of rotation of the respective arm. Rotating the arms causes each arcuate anchor to move in a circular fashion such that when each arm is moved from an open position to a closed position the respective anchor is moved to engage and move through the cardiac tissue and thereby secure the lead to the heart.

11 Claims, 4 Drawing Sheets

EPICARDIAL LEAD HAVING DUAL ROTATABLE ANCHORS

BACKGROUND OF THE INVENTION

1. Field of the Invention

This invention relates to leads for providing electrical signals to a human organ, such as a heart, and more particularly, to an epicardial lead adapted for quick attachment to the heart without extensive operative procedures to suture or connect the epicardial lead to the heart tissue surface.

2. Description of the Prior Art

Heart leads are in widespread use for providing electrical stimulus signals from a pacer device to a patient's heart. In a great majority of the cases where pacers are implanted within a patient on a permanent basis, intracardiac leads are used wherein the lead is introduced into the heart through a convenient vein. This procedure avoids the requirement of having to establish direct access to the heart itself. Such leads also avoid the trauma of actually inserting the lead into the heart wall. The endocardial lead as disclosed in U.S. Pat. No. 4,506,680 to Stokes has proven very successful for use in a large majority of cases.

In a certain percentage of cases, however, it is deemed necessary or desirable to use an external or epicardial lead, wherein the electrode or electrodes are mechanically inserted into the epicardium. In this arrangement, it is necessary that the insertion be made with a minimum of trauma but yet be absolutely secure so that good electrical contact is maintained with the heart. Historically, one form of such epicardial lead has involved actually suturing the lead onto the heart wall to thereby insure the required security. This has the great disadvantage, however, of increasing the complexity of the operative procedure required to implant such a lead.

To overcome the difficulties and complexities presented by use of a sutured epicardial lead, the medical device industry has developed a screw-in epicardial lead. This lead consists of a helical coil which is screwed into the heart wall. Examples of such a lead are disclosed in U.S. Pat. No. 3,416,534 to Quinn and U.S. Pat. No. 3,472,234 to Tachick. This type of lead, however, requires sufficient room to approach the heart wall from a direction more or less perpendicular to the surface to enable the helical coil to be screwed directly into the heart muscle. Even if a perpendicular approach is not required, the physician must still have sufficient access to the heart so as to be able to push the helical coil tip into the epicardium and rotate it.

An alternative to a screw-in lead may be seen in U.S. Pat. No. 4,177,818 to DePedro which discloses an epicardial electrode constructed from a pliable material and having a series of fixation prongs perpendicular to the body. This lead, however, requires the use of a tool or instrument to deform the electrode body back against itself in order to attach it to the heart surface. A variation on a such flexible epicardial lead is disclosed in U.S. Pat. No. 4,144,890 to Hess which shows a lead which must be flexed forward with a tool, rather than backward, against itself in order to insert it into the epicardium.

While these leads have enjoyed a reasonable success to date, there remains a need for a simpler type of epicardial lead which reduces the procedures and tools required of the physician to secure the lead to the heart. The need is to find an epicardial lead which increases the simplicity of the procedure, in contrast to recent designs which have increased the complexity of the procedure and have required specific additional instruments or tools. There is thus a great need for a simple epicardial lead which may be manually secured by the surgeon with a minimum of procedure and with a minimum of access to the heart wall and without the need of specific additional instruments or tools.

SUMMARY OF THE INVENTION

It is an object of the invention to provide an epicardial lead which permits the securing of such lead to the epicardium of a patient's heart or to another organ of the patient, which lead is simple to use, provides a highly secure fixation, and does not require an elaborate engaging tool.

It is another object of this invention to provide an epicardial lead which may be attached to a patient's heart without the need for suturing, and which is of a design which may be easily and reliably fixed to the heart without requiring additional procedures heretofore used to gain access to the heart to attach a screw-in type lead.

It is a further object of this invention to provide an electrode adopted for quick and secure manual fixation to a patient's heart so that when said lead is fixed it is not subject to lateral, vertical or rotational movement relative to the heart.

In accordance with the above objects there is provided an epicardial lead having an electrode extending from the bottom thereof in combination with an anchoring system adapted to be inserted into the patient's heart after prior insertion of the electrode, whereby the lead is secure and invulnerable to movement due to lateral, vertical or rotational movement of the heart wall itself. In the preferred embodiment the epicardial lead comprises an electrode body having two oppositely disposed arms, each arm fixed for rotation, each arm having an arcuate anchor mounted to the bottom surface, each arcuate anchor having as the center of the arcuate shape the axis of rotation of the respective arm. Through such a configuration manual rotation of the arms causes the arcuate anchor to move in a circular fashion such that when the arm is moved from an open position to a closed position the respective anchor is moved to engage and move through the cardiac tissue and thereby secure the electrode body and thus the electrode in place.

DESCRIPTION OF THE PREFERRED EMBODIMENT

Figure 1:
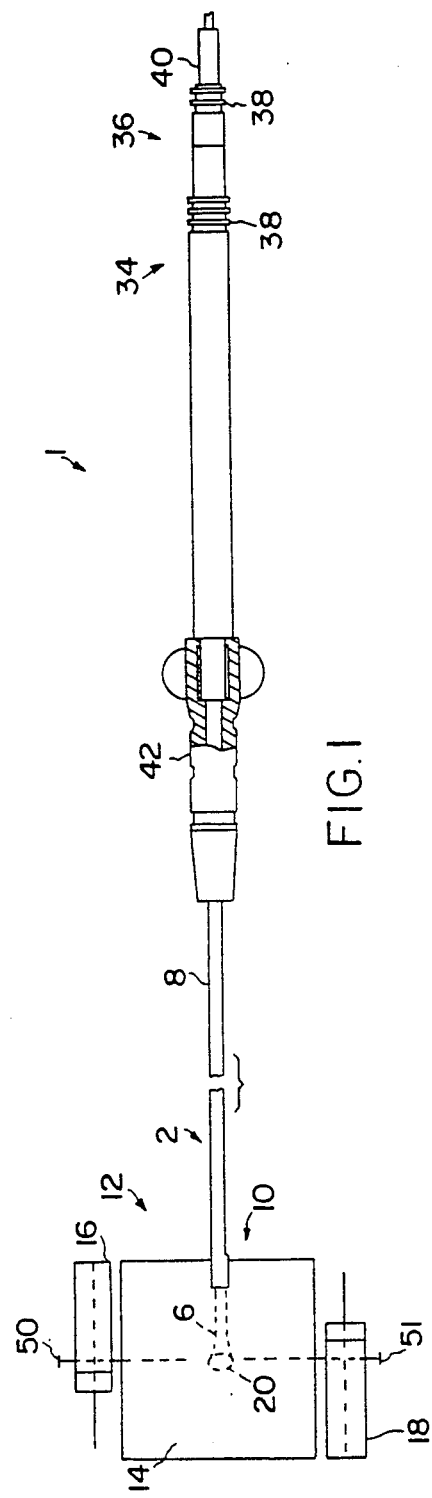
FIG. 1 is a plan view of a lead constructed in according to the present invention.
Figure 2:
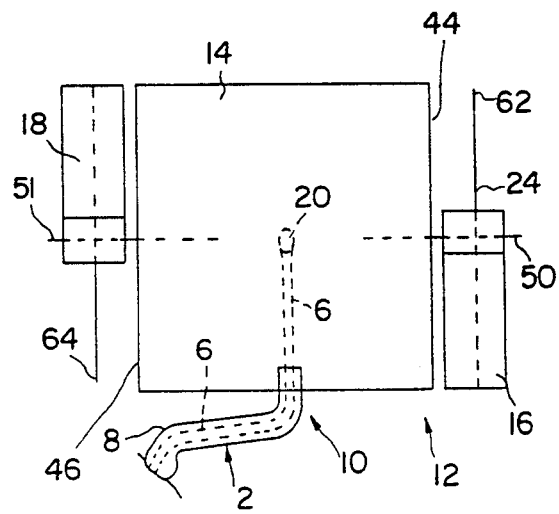
FIG. 2 is a plan view of the top side of an electrode assembly according to the present invention.
Figure 3:
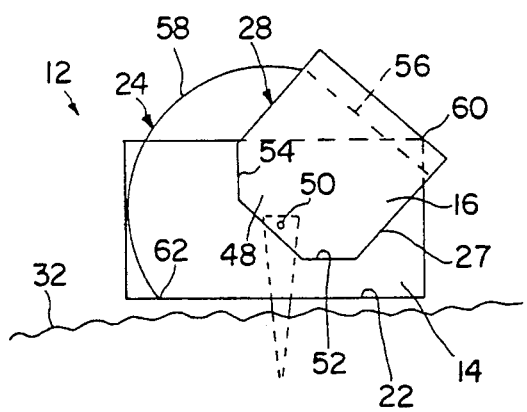
FIG. 3 is a side plan view of an electrode assembly according to the present invention in the open position.
Figure 4:
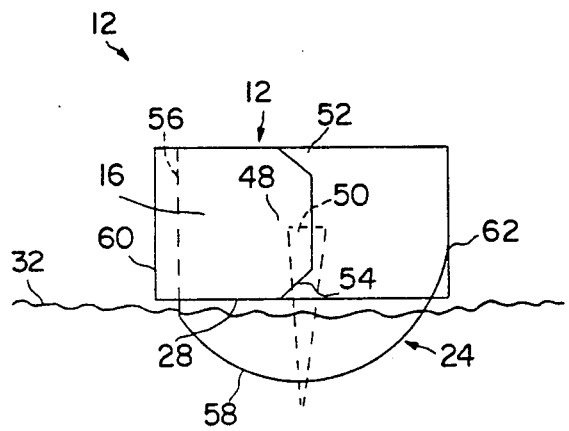
FIG. 4 is a side plan view of an electrode assembly according to the present invention in the closed position.

Referring to FIG. 1, an epicardial lead 1 constructed according to the present invention is shown. As seen, the lead 1 comprises an elongated connector cord 2 and an electrode assembly 12. The connector cord 2 comprises a standard arrangement of a coiled conductor 6 or conductors encased in a suitable insulating cover 8 of a bio-compatible material, such as silicone or a urethane material. At the distal end 10 of elongated connector cord 2, as shown, the electrode assembly 12 is located. As seen in FIGS. 2-4 electrode assembly 12 is constructed from electrode body 14 having two arms 16, 18. The electrode body 14 has an electrode 20 extending from its bottom surface 22. Each arm 16, 18 has an arcuate anchor 24, 26 extending from each respective bottom surface 28, 30 as best seen in FIGS. 3 and 4. Each arcuate anchor 24, 26 has as the center of the arcuate shape the axis of rotation of the respective arm 16, 18. Rotation of the arms therefore causes each arcuate anchor 24, 26 to move in a circular fashion such that when the respective arm is moved from an open position to a closed position the respective anchor is moved to engage and move through the cardiac tissue 32 and thereby secure the electrode body 14 and thus the electrode 20 in place.

FIG. 1 illustrates a plan view of an exposed lead constructed in accordance with the present invention. It should be noted, however, that the relative proportions of lead 1, and especially electrode assembly 12 are not shown to scale. The lead 1 includes an elongated connector cord 2 comprising a length of coiled conductor 6 and an insulative cover 8 as is well known in the art. Insulative cover 8 may be fabricated of any flexible biocompatible and biostable insulator especially silicone rubber or polyurethane. At the proximal end 34 of elongated connector cord 2, terminal assembly 36 is adapted to couple lead 1 to an implantable pulse generator (not shown.) Terminal assembly 36 is provided with sealing rings 38 and a terminal pin 40, all of a type known in the art. An anchoring sleeve 42 (shown partially in cross-section) slides over insulative cover 8 and serves as a point for suturing elongated connector cord 2 to body tissue in a fashion known in the art. Anchoring sleeve 42 and terminal assembly 36 are preferably fabricated of silicone rubber, although they may also be constructed of any other suitable biocompatible material known in the art. The specific design and construction of the elongated connector cord 2 and terminal assembly 36 are not within the scope of the present invention. Further detail and description of the construction of an elongated connector cord 2 and terminal assembly 36 suitable for use with the present invention may be seen, for example, in Daglow et al. U.S. Pat. Nos. 5,070,605 and 4,898,173; Doan et al., U.S. Pat. No. 5,007,435; Hess, U.S. Pat. No. 4,572,605; Peers-Trevarton, U.S. Pat. No. 4,469,104; and O'Neil, U.S. Pat. No. 4,258,725, all incorporated herein by reference.

As best seen in FIG. 2 electrode assembly 12 is fixed to distal end 10 of elongated connector cord 2. Electrode assembly 12 comprises electrode body 14 and arms 16, 18. In the preferred embodiment, electrode body 14 is molded directly to distal end 10 of elongated connector coil 2. Electrode body 14 is molded from HYSOL casting compound manufactured by Dexter Electronics of Olean, New York, although other biocompatible materials may also be used such as a polysulfone or a rigid polyurethane.

Figure 5:
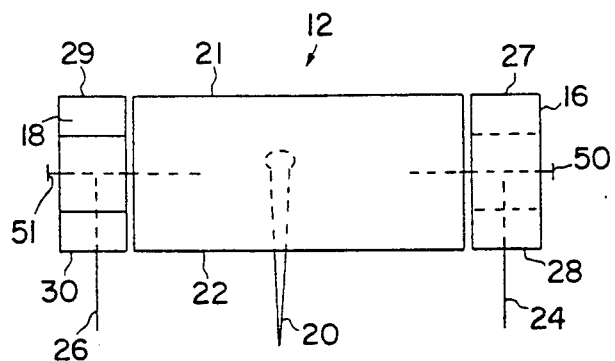
FIG. 5 is a frontal plan view of an electrode assembly according to the present invention.

Mounted to the bottom surface 22 of electrode body 14, as seen in FIG. 5, is electrode 20. Electrode 20 is preferably constructed from a platinum-iridium alloy. Electrode 20 is suitably connected to the coiled conductor 6 of elongated connector cord 2 to provide the necessary mechanical and electrical contact between electrode 20 and terminal assembly 36. The electrode 20 is shaped to actively fix into the cardiac tissue 32. In the preferred embodiment a prong electrode 20, introduced directly into cardiac tissue 32, is shown. Of course other types of electrode configurations may be used, such as a hook-shaped prong or a flat pad, which does not puncture the cardiac tissue.

Figure 6:
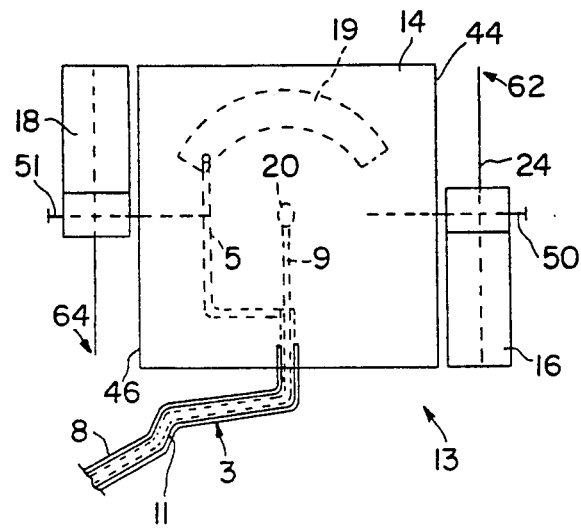
FIG. 6 is a plan view of the top side of an alternate embodiment of an electrode assembly according to the present invention.
Figure 7:
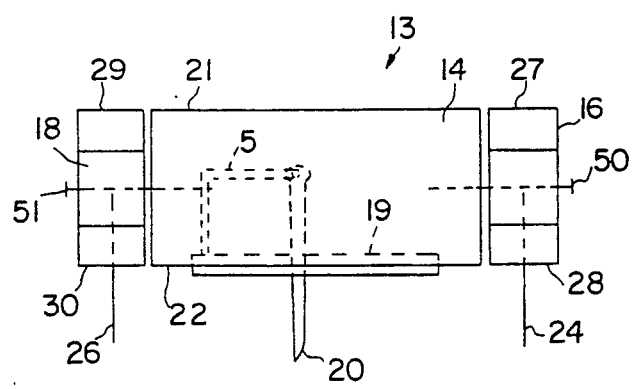
FIG. 7 is a frontal plan view of an alternate embodiment of an electrode assembly according to the present invention.

A further embodiment of the present invention is shown in FIGS. 6 and 7. As seen a bipolar electrode assembly 13 is constructed in a similar fashion as the unipolar electrode assembly 12 discussed above and to the extent possible, the same numerals will be employed to designate the same or equivalent elements of this embodiment of the epicardial lead. Electrode assembly 13 comprises electrode body 14 and arms 16, 18 and is attached to tissue in a manner similar to the unipolar electrode assembly 12 described above. The significant difference between the unipolar electrode assembly 12 described above and the bipolar electrode assembly 13 is the presence of secondary or anode electrode 19. Secondary or anode electrode 19 is spaced apart from electrode 20 and molded into, in the preferred embodiment, bottom surface 22 of electrode body 14. As shown anode electrode 19 protrudes from bottom surface 22, although other configurations, such as a flush electrode or a penetrating electrode, may also be used. In addition, although a semicircle anode electrode 19 is shown other electrode configurations may further be used, such as circular, linear, etc. In addition, anode electrode 19 may further be incorporated with an arcuate anchor 24, 26. The specific configuration of anode electrode 19 used is not within the scope of the present invention. Bipolar electrode assembly 13 further is connected to the distal end of multicoil connector cord 3. Multicoil connector cord 3 comprises a pair of multifilar, commonly wound, separately insulated coils 5, 9 as is well known in the art. Coils 5, 9 are insulated from one another by inner insulative cover 11. Inner insulative cover 11 is preferably made from, like insulative cover 8, a bio-compatible material, such as silicone or a urethane material. As seen inner coil 9 is connected to electrode 20, as described above. Outer coil 5 is connected to secondary or anode electrode 19. The specific construction of multicoil connector cord 3 used is not within the scope of the present invention.

The present invention may further include the use of asteroid or other drug with either or both electrodes 19, 20. Electrode 19, 20 may be configured to allow the drug to be eluted through and/or around in order to reach the endocardial or myocardial cells proximate thereto and reduce the acute and chronic inflammation occasioned by the cellular foreign body and physical irritation response the electrode assembly. As described in Stokes, U.S. Pat. No. 4,506,680 and related Medtronic U.S. Pat. Nos. 4,577,642; 4,606,118 and 4,711,251, mentioned above and herein incorporated by reference, asteroid eluting electrode is fabricated from a body compatible electrically conductive material with or without specific steroid eluting passages but generally with a porous structure either throughout the body of the electrode or at its surface. The porosity of the electrode surface or body provides a large surface area for sensing whereas the overall dimension or shape of the exposed electrode defines a comparatively smaller surface area for stimulation. The porous structure thus presents a microscopic (or "fractal") large surface area for sensing and a macroscopic or geometrically measured very small surface area for stimulation. Acceptable electrode materials and the associated fabrication techniques employed to achieve the micro-porous structure, as well as the porosity of that structure are all set forth in the aforementioned prior art patents and in the Richter et al., U.S. Pat. No. 4,773,433; Heil Jr. et al., U.S. Pat. No. 4,819,661; Thoren et al., U.S. Pat. No. 4,149,542; Robblee, U.S. Pat. No. 4,677,989; Heil Jr. et al., U.S. Pat. No. 4,819,662; Mund et al., U.S. Pat. No. 4,603,704; Skalsky et al., U.S. Pat. No. 4,784,161; Szilagyi, U.S. Pat. No. 4,784,160, herein incorporated by reference and other patents and literature in the prior art.

Attached at opposing sides 44, 46 of electrode body 14 are arms 16, 18. For simplicity of description arm 16 will be described in detail. Arm 18 is identical to arm 16 although it is mounted on the opposite side of electrode body 14 and rotates from the open position to the closed position in an opposite direction. Arm 16 is molded, like electrode body 14, from HYSOL casting compound manufactured by Dexter Electronics of Olean, New York, although other bio-compatible materials may also be used such as a polysulfone or a rigid polyurethane. Proximate to end 48 of arm 16 is mounted by pin 50 to rotate thereabout. As seen in FIGS. 3 and 4 corners 52, 54 of end 48 of arm 16 are rounded. This permits arm 16 to be rotated when bottom surface 22 of electrode body 14 is in contact with cardiac tissue 32, or any other organ, without scrapping or digging into tissue as it would if corners of end 48 were square.

Mounted to bottom surface 28 of arm 16 is anchor 24. Anchor 24 has essentially two portions: mounting portion 56 and anchoring portion 58. Mounting portion 56 is essentially straight and, in the preferred embodiment, molded directly into arm 16 proximate to end 60. Anchoring portion 58 is essentially arcuate and, in the preferred embodiment, follows a curve having as an axis pin 50 which mounts arm 16 to electrode body 14. Through such a configuration then, anchoring portion 58 follows a circular path as arm 16 is rotated. In the preferred embodiment anchor 24 is constructed from a platinum-iridium alloy.

As seen in FIGS. 2 and 5, arms 16, 18 are mounted to opposite sides 44, 46 of electrode body 14 by pins 50, 51 so that each is rotated between the open and closed position in opposite directions. This feature provides additional security to the mounting of lead 1 into cardiac tissue as cardiac motion tending to dislodge arm 16 will equally tend to further lodge arm 18 and vice versa.

Electrode assembly 12 is attached to cardiac tissue 32 as follows. Arms 16, 18 are moved to the open position as shown in FIG. 3. Arms 16, 18 are configured so they may be manipulated by hand and do not require use of special tools. Tips 62, 64 of arms 16, 18 are preferably sharpened. In the open position each anchor 24, 26 is positioned above bottom surface 22 of electrode body 14, i.e. tips 62, 64 of anchors 24, 26 are above bottom surface 22. Electrode assembly 12 is next positioned so that the bottom surface 22 of electrode body 14 abuts against cardiac tissue 32 and electrode 20, as shown in the preferred embodiment, engages into cardiac tissue 32.

Electrode assembly 12 is secured to cardiac tissue 32 by rotating each respective arm 16, 18 in each respective direction so that each respective anchor 24, 26 engages into cardiac tissue 32. Arm 16 is rotated to the closed or secured position, as seen in FIG. 4, so that top surface 27 of arm 16 is flush with top surface 21 of electrode body 14 and tip 62 of anchor 24 is completely clear of cardiac tissue 32. It has been found that in order to reliably secure the lead 1 to the heart so that heart movement does not dislodge the lead 1, the configuration of anchors 24, 26 be such that when the arms 16, 18 are in the closed position the tip of each anchor be approximately perpendicular to the surface of the heart. For additional security, arms 16, 18 may be secured in the closed position by a member (not shown) mounted or glued to top surface 21 of electrode body 14.

While the embodiment of the present invention has been described in particular application to an epicardial lead, it will be understood the invention may be practiced in lead and other electrode technologies where the aforementioned characteristics are desirable, including neurological and muscle stimulation applications.

The invention has been described in detail with particular reference to the preferred embodiment thereof, but it will be understood variations and modifications can be effected within the scope of the following claims.

What is claimed is:

1. An epicardial lead adapted for attaching to a heart comprising:
    an insulated conductor having proximal and distal ends; an electrical connector connected to said proximal end of said conductor
    a body connected to said conductor, said body including a non-conductive an electrode electrically connected to said distal end of said conductor, arm mounted to said body, said arm rotatable between a first position and a second position about a first axis, said arm having an anchor, said anchor shaped to engage said heart and attach said lead thereto when said arm is rotated from said first position to said second position.

2. A lead according to claim 1 further comprising said body having a non-conductive second arm said second arm having an anchor mounted thereto.

3. A lead according to claim 2 further comprising said body having a first surface and a second surface, said second surface being opposite said first surface, said arms mounted to said opposite surfaces of said body.

4. A lead according to claim 2 wherein said second arm rotates about a second axis, wherein said first and second said arms rotate in opposite directions to engage said heart.

5. A lead according to claim 4 wherein said first and second axes of rotation of said arms are coaxial.

6. A lead according to claim 4 further comprising each said anchor having a mounting portion and an anchoring portion, said mounting portion mounted in each said respectively arm, said anchoring portion having an arcuate shape having as its center said respective axis.

7. A device for anchoring a lead to an organ comprising:
    a body, said body having a first surface and a second surface, a first arm mounted to said first surface of said body, said first arm rotatable between an open position and a closed position about a first axis as first anchor mounted to said first arm, a second arm mounted to said second surface of said body, said second arm rotatable between an open position and a closed position about a second axis, a second anchor mounted to said second arm, wherein said first anchor and said second anchor are shaped to engage into said organ and anchor said lead thereto when said first arm is rotated to said closed position and said second arm is rotated to said closed position.

8. A device according to claim 7 wherein said first arm is rotatable about said first axis in a first direction between said open position and said closed position and said second arm is rotatable about said second axis in a second direction between said open position and said closed position wherein said first direction is opposite said second direction.

9. A device according to claim 8 wherein said first axis is coaxial with said second axis.

10. A device according to claim 7 further comprising said first anchor having a first mounting portion and a first anchoring portion, said first mounting portion mounted in said first arm, said first anchoring portion having an arcuate shape having as its center said first axis.

11. A device according to claim 7 further comprising said second anchor having a second mounting portion and a second anchoring portion, said second mounting portion mounted in said second arm, said second anchoring portion having an arcuate shape having as its center said second axis.

* * * * *